United States Patent [19]

Dengel

[11] 4,115,432
[45] Sep. 19, 1978

[54] METHOD FOR MAKING BASICALLY-SUBSTITUTED PHENYLACETONITRILES

[75] Inventor: Ferdinand Dengel, Wilhelmsfeld, Fed. Rep. of Germany

[73] Assignee: Knoll AG., Ludwigshafen am Rhein, Fed. Rep. of Germany

[21] Appl. No.: 812,898

[22] Filed: Jul. 5, 1977

[30] Foreign Application Priority Data

Jul. 12, 1976 [DE] Fed. Rep. of Germany ....... 2631222

[51] Int. Cl.² ............................................ C07C 121/78
[52] U.S. Cl. ............................ 260/465 E; 260/465 F; 260/465 G; 260/465 R
[58] Field of Search ..................... 260/465 E

[56] References Cited

U.S. PATENT DOCUMENTS

| 3,261,859 | 7/1966 | Dengel | 260/465 E |
| 3,262,977 | 7/1966 | Harsanyi et al. | 260/570 |

Primary Examiner—Dolph H. Torrence
Attorney, Agent, or Firm—Curtis, Morris & Safford

[57] ABSTRACT

A method is disclosed for making a basically-substituted phenylacetonitrile of the formula

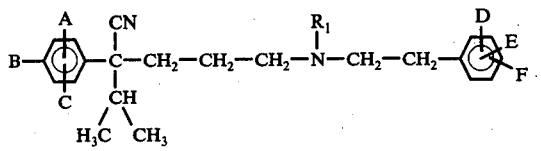

which comprises hydrolyzing a nitriloaldehyde acetal of the formula

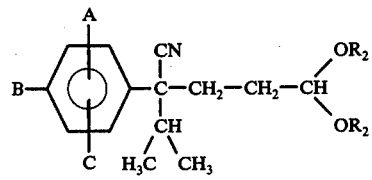

with aqueous acid to obtain a nitriloaldehyde of the formula

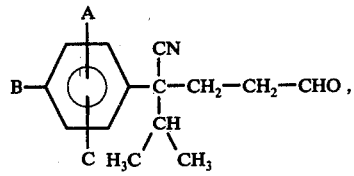

and then subjecting said nitriloaldehyde to a hydrogenating condensation with an amine of the formula

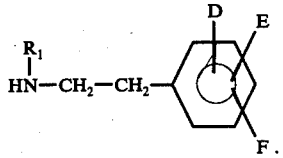

2 Claims, No Drawings

METHOD FOR MAKING BASICALLY-SUBSTITUTED PHENYLACETONITRILES

The present invention relates to a method for the preparation of basically-substituted phenylacetonitriles.

These substances, in particular α-isopropyl-α-[(N-methyl-N-homoveratryl)-γ-aminopropyl)]-3,4,-dimethoxyphenylacetonitrile (Verapamil), are suitable for the treatment of diseases of the coronary blood vessels. A number of methods are already known for their preparation.

According to the present invention, a new method for the preparation of the aforementioned compounds has been found, which method proceeds smoothly and with good yields.

According to the present invention, basically-substituted phenylacetonitriles of the following formula I

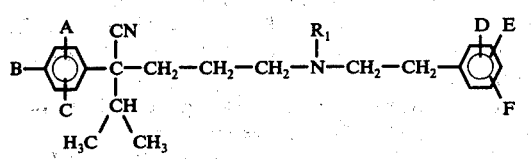

wherein A, C, D, E, and F are hydrogen, halogen or lower alkoxy, B is halogen or lower alkoxy, and $R_1$ is lower alkyl, are prepared by treating a nitriloaldehyde acetal of the following formula II

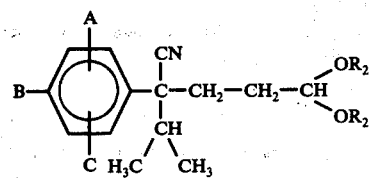

wherein A, B, and C have the aforementioned meaning and $R_2$ is lower alkyl, with aqueous acid and subsequently subjecting the nitriloaldehyde so obtained, of the formula III

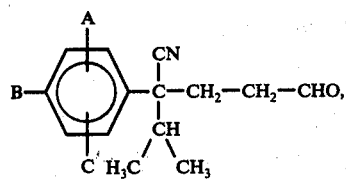

to a hydrogenating condensation with an amine of the formula IV

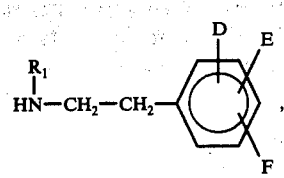

wherein D, E, F, and $R_1$ have the aforementioned meaning.

Nitriloaldehyde acetals of the formula II are obtained from the corresponding nuclearly-substituted α-isopropyl benzyl cyanides by condensation with acetals of the formula V

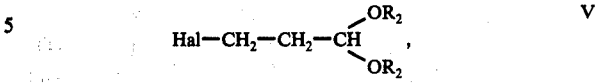

wherein $R_2$ has the aforementioned meaning and Hal is halogen.

The hydrolysis of acetals of the formula II can take place in suitable organic solvents employing diluted aqueous acids such as sulfuric acid, hydrochloric acid, acetic acid, oxalic acid, or tartaric acid. It is not necessary to isolate the nitriloaldehydes which are formed in pure form. Suitably, they are subjected in their raw product form to a hydrogenating condensation with an amine of the formula IV. The reaction is particularly successful employing nickel- or cobalt-containing catalysts, such as Raney nickel. If the reaction partners do not contain halogen, noble metal catalysts such as Pd/C and $PtO_2$ are also suitable. The hydrogenating condensation takes place at normal pressures (760 mm Hg of $H_2$) at room temperature or a temperature slightly thereabove with good yields. The reaction is preferably carried out in lower alcohols or glacial acetic acid.

Nitriloaldehyde acetals of the formula II can be prepared by the condensation of corresponding nuclearly-substituted α-isopropyl benzyl cyanides with β-halogen propionaldehyde dialkyl acetals in the presence of lithium amide or sodium amide or of a metal organic compound such as butyl lithium or phenyl sodium. As solvents, tetrahydrofuran, dioxane, benzene, and toluene are suitable, for example.

The yields of the new process are high. They amount to about 85 – 95 percent in each reaction step. As a rule, yields of even 75 – 85 percent are obtained calculated on the substituted α-isopropyl benzyl cyanide. These values lie far above those which have heretofore been obtained for the preparation of the aforementioned compounds. Further, the new process is substantially easier to carry out than are the known methods.

A better understanding of the present invention and of its many advantages will be had by referring to the following specific examples, given by way of illustration.

EXAMPLE 1

(a)

573 g (2.62 mol) of α-isopropyl veratryl cyanide and 481 g (1.1 × 2.62 mol) of β-chloropropionaldehyde diethyl acetal are dissolved in 2.7 l of dry toluene with heating. 393 g of a 30 percent sodium amide suspension in toluene (117.6 g or 1.15 × 2.62 mol of $NaNH_2$) are added dropwise to the boiling solution with vigorous stirring during the course of an hour. After 3 hours the reaction solution is cooled and washed once with 3 l of an ice-water mixture and subsequently washed twice with 1 l of water. The toluene phase is dried and concentrated. Distillation of the residue gives 772 g of α-isopropyl-α-(γ-diethoxypropyl)-veratryl cyanide, b.p. = 160° – 163° C./0.3 mm Hg, $n_D^{25}$ = 1.5000, yield = 84.3%.

(b) 445 g (1.274 mol) of the substance obtained according to (a) are dissolved in 2.9 l of acetone. Over 45 minutes, 127.5 g (1.1 × 1.274 mol) of oxalic acid in 1150 ml of water are added dropwise thereto with stirring. The solution is left to stand for 3 hours at 40° C., subsequently cooled to 5°–10° C., and adjusted to a pH of 6.0 with a saturated aqueous potassium carbonate solution. The precipitated potassium oxalate is filtered off and the acetone is removed from the filtrate in a rotary evaporator. The oily aldehyde which separates thereby is taken up in diethyl ether and dried over potassium carbonate. After evaporation, 413 g of a yellowish oil are obtained which contain 85 percent of α-isopropyl- α-(γ-oxopropyl)-veratryl cyanide, b.p. = 148° – 149° C. (as the semicarbazone). The yield is practically quantitative.

The same result is obtained if one employs 2 percent sulfuric acid in place of the oxalic acid.

(c) 91.1 g of the yellowish oil obtained according to (b) [corresponding to 77.4 g (0.281 mol) of pure α-isopropyl-α-(γ-oxopropyl)-veratryl cyanide] and 54.9 g (0.281 mol) of N-methyl-homoveratryl amine are dissolved in 400 ml of ethanol and hydrogenated with 10 grams of 10 percent palladium-charcoal at 40°–45° C. After conclusion of hydrogen uptake, the catalyst is separated by vacuum filtration and the filtrate is reduced to dryness. The oily residue is dissolved in 500 ml of toluene and washed twice with 250 ml portions of water. The aqueous extracts are discarded. The toluene solution is extracted twice with 150 ml portions of 2 N hydrochloric acid and twice with 150 ml portions of warm water. The aqueous extracts are combined, made alkaline with sodium hydroxide, and extracted with toluene. The toluene extracts are dried, evaporated, and the residue is dissolved in isopropanol. After the introduction of hydrogen chloride gas, 127.0 g of α-isopropyl-α-[(N-methyl-N-homoveratryl)-γ-aminopropyl]-3,4-dimethoxyphenyl acetonitrile hydrochloride separate, m.p. = 139.5°–141.5° C., yield = 92 percent.

If the hydrogenation is carried out with Raney-nickel, Raney-cobalt, or platinum oxide, the yields are 90–95 percent.

EXAMPLE 2

(a)

417.2 g (1.673 mol) of α-isopropyl-3,4,5-trimethoxyphenyl acetonitrile in 830 ml of tetrahydrofurane are added dropwise to a mixture of 557.4 g (2 × 1.673 mol) of β-chloropropionaldehyde diethyl acetal in 1.1 l of tetrahydrofuran and 550 g (2 × 1.673 mol) of a 30 percent sodium amide suspension in toluene during the course of 1 hour at 78° C. After a further 30 minutes, the reaction mixture is cooled and filtered. The filtrate is concentrated to dryness and the residue is recrystallized from hexane.

595.4 g of α-isopropyl-α-(γ-diethoxypropyl)-3,4,5-trimethoxyphenyl acetonitrile are obtained, m.p. = 64.5° – 67° C., yield = 93.8 percent.

(b)

From the aforementioned compound, proceeding analogously to Example 1 (b), α-isopropyl-α-(γ-oxopropyl)-3,4,5-trimethoxyphenyl acetonitrile is obtained in practically quantitative yield, b.p. = 195° – 200° C./0.02 mm Hg.

(c)

The compound obtained according to (b) is hydrogenated and worked up together with N-methyl-homoveratryl amine according to Example 1 (c). Pure α-isopropyl-α-[(N-methyl-N-homoveratryl)-γ-aminopropyl]-3,4,5-trimethoxyphenyl acetonitrile hydrochloride containing water of crystallization already crystallizes from the hot hydrochloric acid extracts. The salt is dehydrated by azeotropic distillation with toluene and the oily residue is dissolved in isopropanol. In the cold, the dehydrated hydrochloride separates from the solution as a white loose crystalline powder, m.p. = 146° - 147.5° C., yield = 91.6%.

Proceeding as in Examples 1 and 2 the following compounds were prepared with corresponding yields:

α-isopropyl-α-[(N-methyl-N-β-phenylethyl)-γ-aminopropyl]-3,4-dimethoxyphenyl acetonitrile, b.p. = 180° – 195° C./0.005 mm Hg, m.p. = 150° – 151° C. (as the hydrochloride), m.p.= 131° – 133° C. (as the dioxalate);

α-isopropyl-α-[(N-methyl-N-4-chlorophenylethyl)-γ-aminopropyl)]-3,4-dimethoxyphenyl acetonitrile, b.p. = 220° – 225° C./0.03 mm Hg, m.p. = 162° – 163° C. (as the hydrochloride);

α-isopropyl-α-(N-methyl-N-β-phenylethyl-γ-aminopropyl)-3,4,5-trimethoxyphenyl acetonitrile, b.p. = 180° C./0.005 mm Hg, m.p. = 156° – 159° C. (as the hydrochloride).

What is claimed is:

1. A method for making a basically-substituted phenylacetonitrile of the formula

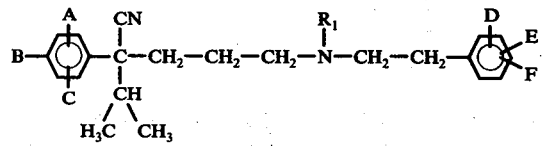

wherein A, C, D, E, F are hydrogen, halogen, or lower alkoxy, B is halogen or lower alkoxy, and $R_1$ is lower alkyl, which method comprises hydrolyzing a nitriloaldehyde acetal of the formula

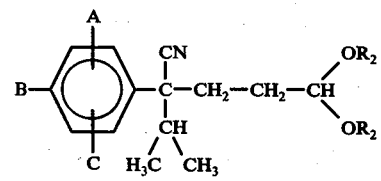

wherein A, B and C have their aforementioned meanings and $R_2$ is lower alkyl, with aqueous acid to obtain a nitriloaldehyde of the formula

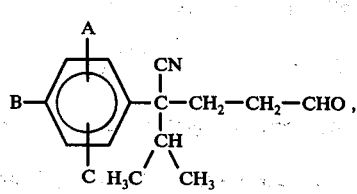

and then subjecting said nitriloaldehyde to a hydrogenating condensation with an amine of the formula

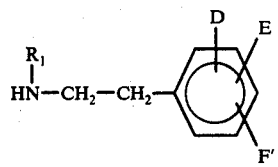

wherein D, E, F and $R_1$ have their aforementioned meanings.

2. A method as in claim 1 wherein said nitriloaldehyde acetal is obtained by condensing the corresponding nuclearly-substituted α-isopropylbenzylcyanide with an acetal of the formula

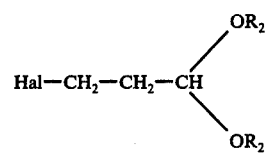

wherein $R_2$ has the meaning given in claim 1 and Hal is halogen.

* * * * *